(12) United States Patent
Clinton et al.

(10) Patent No.: US 6,962,787 B2
(45) Date of Patent: Nov. 8, 2005

(54) DIAGNOSTIC METHOD FOR A TRANSMISSIBLE SPONGIFORM ENCEPHALOPATHY OR A PRION DISEASE

(75) Inventors: Michael Clinton, Roslin (GB); Gino Miele, Roslin (GB); Jean Catherine Manson, Newbury (GB)

(73) Assignee: Roslin Institute (Edinburgh), Scotland (GB)

( * ) Notice: Subject to any disclaimer, the term of this patent is extended or adjusted under 35 U.S.C. 154(b) by 0 days.

(21) Appl. No.: 09/999,305

(22) Filed: Oct. 31, 2001

(65) Prior Publication Data

US 2002/0164661 A1 Nov. 7, 2002

(30) Foreign Application Priority Data

Oct. 31, 2000 (GB) .............................................. 0026604

(51) Int. Cl.$^7$ ......................... G01N 33/53; A01N 63/00; A61K 39/395; A61K 39/00
(52) U.S. Cl. ..................... 435/7.1; 424/93.7; 424/93.71; 424/93.72; 424/93.73; 424/130.1; 424/158.1; 424/184.1; 424/198.1; 436/501
(58) Field of Search ............................. 424/93.7, 93.71, 424/93.72, 93.73, 130.1, 158.1, 184.1, 198.1; 435/7.1; 436/501

(56) References Cited

U.S. PATENT DOCUMENTS 6,110,739 A    8/2000   Keller et al. ................. 435/325

FOREIGN PATENT DOCUMENTS

| WO | WO 00/42165 | 7/2000 | |
|---|---|---|---|
| WO | WO 00/65357 | 11/2000 | .......... G01N/33/68 |
| WO | WO 01/19860 | 3/2001 | ........... C07K/14/00 |

OTHER PUBLICATIONS

Wang, X., et al Preparation and determination of monoclonal antibodies against the proteins related to erythroid differentiation Jiepou Xuebao, vol. 28, No. 2, pp. 187–192, 1997.*

Hochstrasser, et al., "Elevation of Apolipoprotein E in the CSF of cattle affected by BSE" *FEBS Letters,* vol. 416 (2), pp. 161–163 (1997).

Otto, et al., "Elevated Levels of Tau–Protein in Cerebrospinal Fluid of Patients with Creutzfeldt–Jakob Disease" *Neuroscience Letters,* vol. 225 (3), pp. 210–212 (1997).

Beekes, et al., "Western Blot Mapping of Disease–Specific Amyloid in Various Animal Species and Humans with Transmissible Spongiform Encephalopathies Using A High–Yield Purification Method" *Journal of General Virology,* vol. 76 pp. 2567–2576 (1995).

Miele et al., "A Novel Erythroid–Specific Marker of Transmissible Sponigiform Encephalopathies" *Nature Medicine,* vol. 7 (3) pp. 361–364 (2001).

Prusiner, S.B. "Prions." Proc. Nat'l Acad. Sci. USA. 1998; 95(23):13363–83.

Schmerr, M.J. et al. "Use of capillary electrophoresis and fluorescent labeled peptides to detect the abnormal prion protein in the blood of animals that are infected with a transmissible spongiform encephalopathy." J. Chromatogr. A. 1999; 853(1–2): 207–14.

Ikuta, K. et al. "A developmental switch in thymic lymphocyte maturation potential occurs at the level of hematopoietic stem cells." Cell. 1990; 62(5): 863–74.

Sperling Biomedical Foundation, "Index to Science Archives," Internet: http://www.mad–cow.org/00/sci_archive_frame.html (downloaded Feb. 12, 2002).

* cited by examiner

Primary Examiner—Rodney P Swartz
(74) Attorney, Agent, or Firm—William Cutler Pickering; Hale and Dorr LLP

(57) ABSTRACT

A method is provided for the diagnosis of a transmissible spongiform encephalopathy (TSE) or prion disease in an animal which comprises assaying a sample obtained from said animal to determine the number of hematopoietic cells of the erythroid, megakaryocyte or platelet cell lineages in the sample or an expression product thereof.

13 Claims, 10 Drawing Sheets

(a)

<u>CAGCAAGAGC</u> TGAGTACTCT GGGCAGCCAG TTTCTAGCCA AATACAGGAC CTTTCTGAAG
TCCAAAGAGC CCCCAAGCAA TACACTGCCC TCCTCATAAC TTAAAGGGTC TGGGCATCAT
GTCTTAGAAC CCCAAACACT CGGCTCTGTG TTATATCTTC AGACCGTTCT CCCAAGATGT
TGCTGTACTT TGACATGCCA ATAAAGACCA AATACT<u>CAAA AAAAAAAAAA</u>

(b)

(a) Murine EDRF nucleotide sequence

```
  1  tcaaaccccg aggattgtgg atgaggcggg ctcagcacca ttagacttga
 51  agatggcccc ttttcagagc aataaggatc tgatctccac agggataaag
101  gagtttaatg ttctgctgga tcagcaggtc tttgatgatc ctctgatctc
151  tgaagaagac atggtgattg tggttcatga ctgggtgaac ttgtacacca
201  actattacaa gaagctcgtg catggggagc aggaggagca agacagggcc
251  atgacagaat ccagcaaga gctgagtact ctgggcagcc agtttctagc
301  caaatacagg accttctga agtccaaaga gcccccaagc aatacactgc
351  cctcctcata acttaaaggg tctgggcatc atgtcttaga accccaaaca
401  ctcggctctg tgttatatct tcagaccgtt ctcccaagat gttgctgtac
451  tttgacatgc aataaagac caaatactca aaaaaaaaa aaaaaaaaa
501  aaaaa
```

(b) Human EDRF nucleotide sequence

```
  1  ggggacagag agattcacgc accctcaaga gtgtgggtga gacatataca
 51  gcctgttaga cctgaaggca gatggctctt cttaaggcca ataaggatct
101  catttccgca ggattgaagg agttcagcgt tctgctgaat cagcaggtct
151  tcaatgatcc tctcgtctct gaagaagaca tggtgactgt ggtggaggac
201  tggatgaact tctacatcaa ctattacagg cagcaggtga caggggagcc
251  ccaagagcga gacaaggctc tgcaggagct tcggcaagag ctgaacactc
301  ttgccaaccc tttcctggcc aagtacaggg acttcctgaa gtctcatgag
351  ctcccgagtc acccaccgcc ctcctcctag ctcagggacc cagcccctcc
401  tctctgagaa actctgacct tcatgtcctt aggctgtgct cctgccactc
451  taccctgaca cctcaataaa gaccagtgct ggttttgttg gaaaaaaaaa
501  a
```

(c) Partial (168 bp) Bovine EDRF Open Reading Frame Sequence

```
  1  gaggaagata tggtgaccgt ggtgaatgac tgggtgagct tttacatcaa
                c            tt
 51  ctattacaag aagcagctgt cgggagagca agacgagcag gacaaggctc 101  tgcaggagtt tcggcaagag ctcaataccc tgtctgcctc tttcctagca
                                                        t
151  aaataccgcc cctttct
        g            c
```

FIG. 3

(a) Mouse EDRF protein amino acid sequence

```
  1 MAPFQSNKDL ISTGIKEFNV LLDQQVFDDP LISEEDMVIV VHDWVNLYTN
 51 YYKKLVHGEQ EEQDRAMTEF QQELSTLGSQ FLAKYRTFLK SKEPPSNTLP
101 SS
```

(b) Human EDRF protein amino acid sequence

```
  1 MALLKANKDL ISAGLKEFSV LLNQQVFNDP LVSEEDMVTV VEDWMNFYIN
 51 YYRQQVTGEP QERDKALQEL RQELNTLANP FLAKYRDFLK SHELPSHPPP
101 SS
```

(c) Partial Bovine EDRF protein amino acid sequence

```
  1 EEDMVTVVND WVSFYINYYK KQLSGEQDEQ DKALQEFRQE LNTLSASFLA
 51 KYRPF
```

FIG. 4

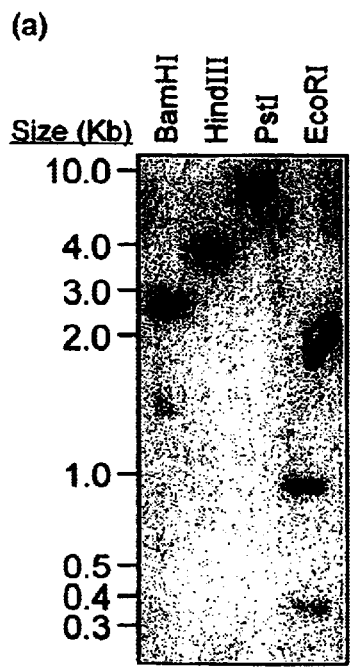
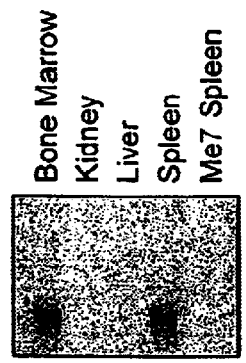
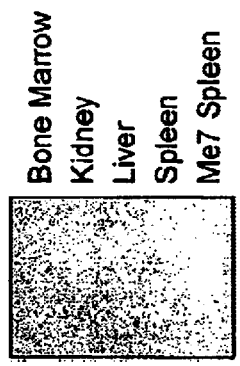

FIG. 5

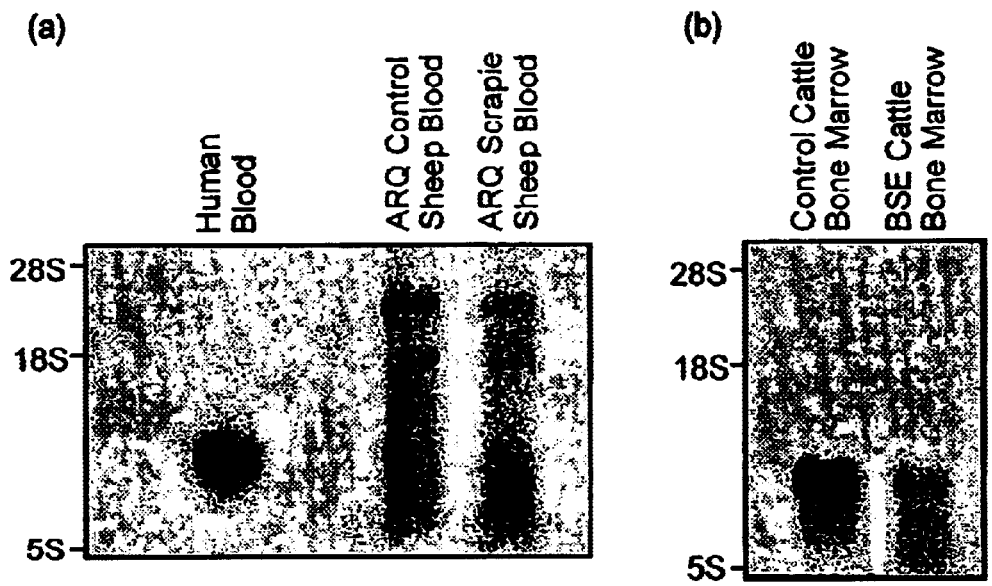

FIG. 8

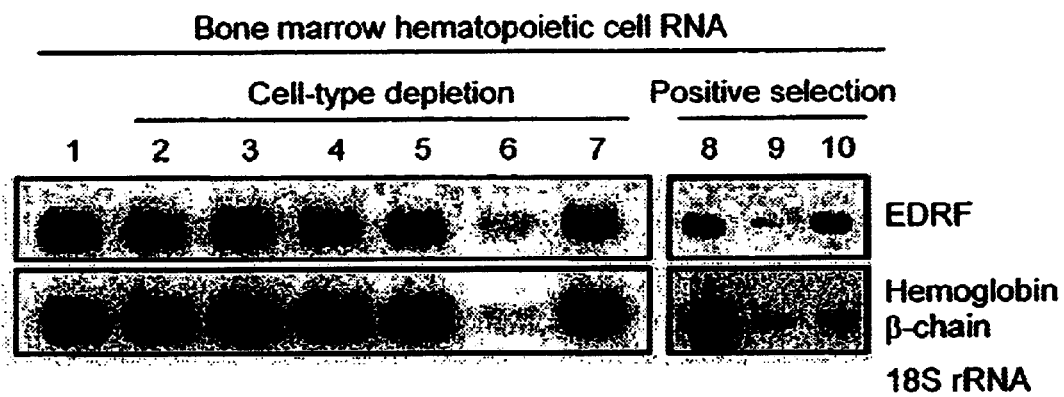

1. Whole Bone marrow.
2. CD3e-depleted bone marrow (thymocytes and circulating T-cells)
3. CD11b-depleted bone marrow (monocytes, granulocytes, macrophages, dendritic cells, NK cells, B-1 cells).
4. CD45R/B220-depleted bone marrow (B-cells at all stages of development).
5. Ly-6G-depleted bone marrow (granulocytes, monocytes, neutrophils).
6. TER-119-depleted bone marrow (all erythroid cells, including erythrocytes, except BFUe/CFUe Cells).
7. Hematopoietic stem cells and BFUe/CFUe-depleted bone marrow.
8. TER-119+ bone marrow cells.
9. CD3+, CD11b+, CD45R+, B220+, Ly-6G+, bone marrow cells.
10. Lineage-negative hematopoietic stem cells (and BFUe/CFUe cells).

FIG. 9

Grid Reference

A1 = E/Meg/Mac/Neut/Mast
A2 = E/Meg/Mac/Neut
A3 = E/Meg/Mac
A4 = E/Meg
A5 = Mac/Neut
A6 = BFU-E
A7 = CFU-E B1 = Mac progenitor
B2 = Neut progenitor
B3 = Meg progenitor
B4 = E
B5 = N
B6 = Mast
B7 = Meg C1 = B cells
C2 = Mac
C3 = T cells
E4 = Stem cells

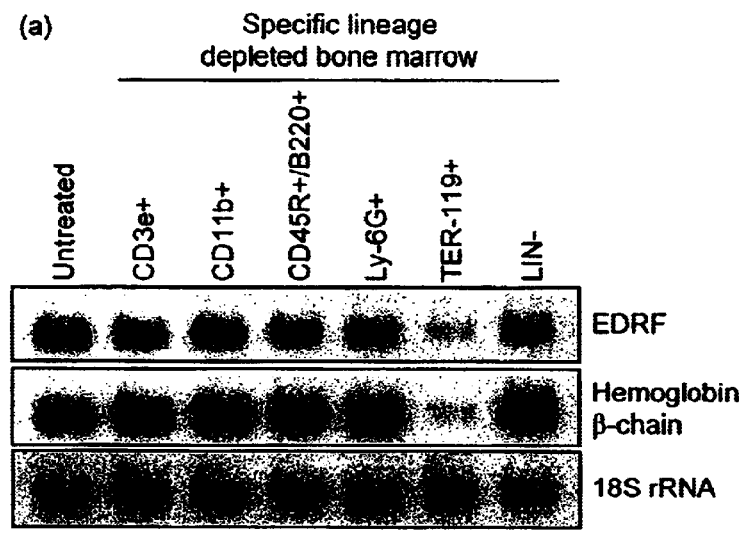
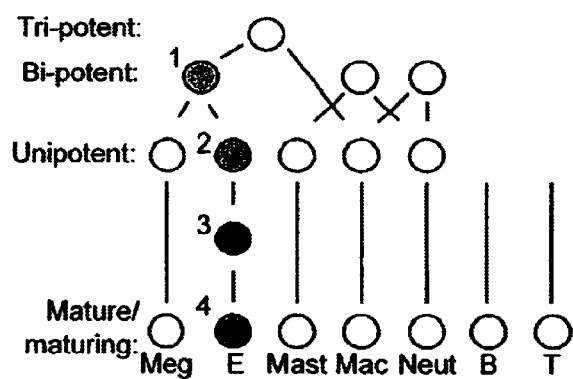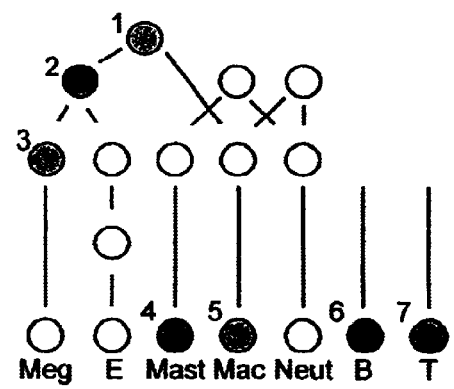
FIG. 11

SEQUENCE LISTING

```
<160> NUMBER OF SEQ ID NOS: 10

<210> SEQ ID NO 1
<211> LENGTH: 230
<212> TYPE: DNA
<213> ORGANISM: Mus musculus

<400> SEQUENCE: 1
cagcaagagc tgagtactct gggcagccag tttctagcca aatacaggac ctttctgaag      60
tccaaagagc ccccaagcaa tacactgccc tcctcataac ttaaagggtc tgggcatcat     120
gtcttagaac cccaaacact cggctctgtg ttatatcttc agaccgttct cccaagatgt     180
tgctgtactt tgacatgcca ataaagacca aatactcaaa aaaaaaaaaa                 230

<210> SEQ ID NO 2
<211> LENGTH: 505
<212> TYPE: DNA
<213> ORGANISM: Mus musculus

<400> SEQUENCE: 2 tcaaacccccg aggattgtgg atgaggcggg ctcagcacca ttagacttga agatggcccc     60
ttttcagagc aataaggatc tgatctccac agggataaag gagtttaatg ttctgctgga    120
tcagcaggtc tttgatgatc ctctgatctc tgaagaagac atggtgattg tggttcatga    180
ctgggtgaac ttgtacacca actattacaa gaagctcgtg catggggagc aggaggagca    240
agacagggcc atgacagaat tccagcaaga gctgagtact ctgggcagcc agtttctagc    300
caaatacagg acctttctga agtccaaaga gcccccaagc aatacactgc cctcctcata    360
acttaaaggg tctgggcatc atgtcttaga accccaaaca ctcggctctg tgtttatatct    420 tcagaccgtt ctcccaagat gttgctgtac tttgacatgc aataaagac caaatactca     480 aaaaaaaaaa aaaaaaaaaa aaaaa                                            505
```

<210> SEQ ID NO 3
<211> LENGTH: 501
<212> TYPE: DNA
<213> ORGANISM: Homo sapiens

<400> SEQUENCE: 3

```
ggggacagag agattcacgc accctcaaga gtgtgggtga gacatataca gcctgttaga      60
cctgaaggca gatggctctt cttaaggcca ataaggatct catttccgca ggattgaagg     120
agttcagcgt tctgctgaat cagcaggtct tcaatgatcc tctcgtctct gaagaagaca     180
tggtgactgt ggtggaggac tggatgaact tctacatcaa ctattacagg cagcaggtga     240
caggggagcc ccaagagcga gacaaggctc tgcaggagct tcggcaagag ctgaacactc     300
ttgccaaccc tttcctggcc aagtacaggg acttcctgaa gtctcatgag ctcccgagtc     360
acccaccgcc ctcctcctag ctcagggacc cagcccctcc tctctgagaa actctgacct     420
tcatgtcctt aggctgtgct cctgccactc taccctgaca cctcaataaa gaccagtgct     480
ggttttgttg gaaaaaaaaa a                                               501
```

<210> SEQ ID NO 4
<211> LENGTH: 167
<212> TYPE: DNA
<213> ORGANISM: Bos sp.

<400> SEQUENCE: 4

```
gaggaagaya tggtgayygt ggtgaatgac tgggtgagct tttacatcaa ctattacaag      60
aagcagctgt cgggagagca agacgagcag gacaaggctc tgcaggagtt tcggcaagag     120
ctcaataccc tgtctgcctc tttcctwgca aartaccgcc ccttyct                   167
```

<210> SEQ ID NO 5
<211> LENGTH: 102
<212> TYPE: PRT
<213> ORGANISM: Mus musculus

<400> SEQUENCE: 5

```
Met Ala Pro Phe Gln Ser Asn Lys Asp Leu Ile Ser Thr Gly Ile Lys
  1               5                  10                  15

Glu Phe Asn Val Leu Leu Asp Gln Gln Val Phe Asp Asp Pro Leu Ile
                 20                  25                  30

Ser Glu Glu Asp Met Val Ile Val His Asp Trp Val Asn Leu Tyr
             35                  40                  45

Thr Asn Tyr Tyr Lys Lys Leu Val His Gly Gln Glu Glu Gln Asp
 50                  55                  60

Arg Ala Met Thr Glu Phe Gln Gln Glu Leu Ser Thr Leu Gly Ser Gln
 65                  70                  75                  80

Phe Leu Ala Lys Tyr Arg Thr Phe Leu Lys Ser Lys Glu Pro Pro Ser
                 85                  90                  95

Asn Thr Leu Pro Ser Ser
            100
```

<210> SEQ ID NO 6
<211> LENGTH: 102
<212> TYPE: PRT
<213> ORGANISM: Homo sapiens

<400> SEQUENCE: 6

```
Met Ala Leu Leu Lys Ala Asn Lys Asp Leu Ile Ser Ala Gly Leu Lys
  1               5                  10                  15
```

```
Glu Phe Ser Val Leu Asn Gln Gln Val Phe Asn Asp Pro Leu Val
                20                  25                  30

Ser Glu Glu Asp Met Val Thr Val Val Glu Asp Trp Met Asn Phe Tyr
        35                  40                  45

Ile Asn Tyr Tyr Arg Gln Gln Val Thr Gly Pro Gln Glu Arg Asp
 50                  55                  60

Lys Ala Leu Gln Glu Leu Arg Gln Glu Leu Asn Thr Leu Ala Asn Pro
 65                  70                  75                  80

Phe Leu Ala Lys Tyr Arg Asp Phe Leu Lys Ser His Glu Leu Pro Ser
                85                  90                  95

His Pro Pro Pro Ser Ser
            100

<210> SEQ ID NO 7
<211> LENGTH: 55
<212> TYPE: PRT
<213> ORGANISM: Bos sp.

<400> SEQUENCE: 7

Glu Glu Asp Met Val Thr Val Val Asn Asp Trp Val Ser Phe Tyr Ile
 1               5                  10                  15

Asn Tyr Tyr Lys Lys Gln Leu Ser Gly Glu Gln Asp Glu Gln Asp Lys
                20                  25                  30

Ala Leu Gln Glu Phe Arg Gln Glu Leu Asn Thr Leu Ser Ala Ser Phe
            35                  40                  45

Leu Ala Lys Tyr Arg Pro Phe
 50                  55

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (9)
<223> OTHER INFORMATION: n is a or g or c or t

<400> SEQUENCE: 8
carcargtnt tyraygaycc                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (15, 18)
<223> OTHER INFORMATION: n is a or g or c or t

<400> SEQUENCE: 9
gargargaya tggtnayngt                                              20

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Primer
```

-continued

```
<220> FEATURE:
<221> NAME/KEY: modified_base
<222> LOCATION: (6)..(9)
<223> OTHER INFORMATION: i
<220> FEATURE:
<221> NAME/KEY: misc_feature
<222> LOCATION: (18, 21)
<223> OTHER INFORMATION: n is a or g or c or t

<400> SEQUENCE: 10
agraannnnc krtayttngc na                                          22
```

DIAGNOSTIC METHOD FOR A TRANSMISSIBLE SPONGIFORM ENCEPHALOPATHY OR A PRION DISEASE

The present invention relates to a new method of diagnosis for a transmissible spongiform encephalopathy (TSE) or a prion disease.

A comprehensive overview of TSE biology can be found in published review format (Prusiner, S. B., Proc. Nat'l Acad. Sci. USA 95 13363–13383 (1998)) and/or on the internet (http:/www.mad-cow.org). Transmissible Spongiform Encephalopathies (TSEs) or Prion diseases are a group of invariably fatal disorders of the central nervous system (CNS), which manifest via genetic, infectious or sporadic mechanisms. They include Scrapie in sheep, Bovine Spongiform Encephalopathy (BSE) in cattle and Kuru, Creutzfeldt-Jacob Disease (CJD), new-variant (nv) CJD, Gerstmann-Straussler Sheinker Syndrome (GSS) and Fatal Familial Insomnia in humans. TSE diseases also manifest in other species such as elk, deer, mink, cats (FSE) and exotic zoo species such as Nyala, Arabian Oryx, Cheetah and greater Kudu. Chronic wasting disease (CWD) has also been identified in deer and elk and it has been suggested that this could also be transmitted to humans.

The TSE diseases are characterized by long, asymptomatic incubation periods followed by a relatively rapid clinical course frequently consisting of neurodegeneration, vacuolation, glial cell proliferation and the deposition of protease-resistant Prion protein$^{Sc}$ (PrP$^{Sc}$), an abnormal isoform of a host-encoded glycoprotein, PrP$^C$. Conversion of normal, proteinase K-sensitive PrP$^C$ into the abnormal, proteinase K-resistant isoform, PrP$^{Sc}$, is a frequent characteristic hallmark of the TSE diseases.

Currently, in the United Kingdom, there is considerable interest in TSE diseases as a result of the BSE epidemic and the subsequent emergence of new-variant CJD in humans; a TSE disease thought to have arisen from BSE and to have crossed the species barrier into humans as a result of BSE-infected tissues entering the human food chain. It is probable that the vast majority of UK citizens have been exposed to the BSE infectious agent. In addition to the problem of natural scrapie in sheep, there is great concern that BSE may also be harboring in sheep at a sub-clinical asymptomatic level, and other agricultural species, as a result of BSE infected material having been present in animal feedstuffs.

The extent to which the UK population is harboring nvCJD, and the proportion which will go on to develop the disease is currently unclear. At present, there is no effective pre-mortem diagnostic means of assessing potential TSE infection in humans or animals. Both in order to remove TSE infected agricultural species from the human food chain, and to assess potential TSE infection in humans, suitable diagnostic methods are desirable, and ideally in easily accessible tissues such as blood. At present, the only disease-specific macromolecule identified is PrP$^{Sc}$. However, PrP$^{Sc}$ is only practically detectable in CNS tissue at post-mortem, although in some TSE diseases it may be detected in tonsil biopsies (Coghlan, A., New Scientist, page 5, (15 Jun. 1996)). It has recently been demonstrated that PrP$^{Sc}$ can be detected in blood of TSE infected animals (Schmerr et al Journal of Chromatography 853 (1-2) 207–214 (1999)). However, this is both a time-consuming and significantly technically demanding procedure, as is the detection of PrP$^{Sc}$ generally. Additionally, PrP$^{Sc}$ is often undetectable in CNS tissue of humans and animals clearly affected by TSE diseases. There is therefore no effective pre-mortem diagnostic means of assessing TSE infection. An ideal diagnostic method should therefore be non-PrP$^{Sc}$-based, and would allow assessment of potential TSE infection in easily accessible tissues such as blood. Such a diagnostic test would ideally allow assessment of TSE infection in live individuals at an early stage such that therapeutic intervention strategies could be implemented.

There have been several published reports of genes which are differentially expressed in CNS tissue of TSE-infected animals. However, to date, there have been no other reports of differential gene expression in spleen, bone marrow or blood of TSE-infected animals. Although blood from TSE-infected animals has been shown to be infectious and the PrP$^C$ protein has been demonstrated to be expressed in several hematopoietic cells there has been no recognition prior to the present invention of the connection between erythroid hematopoietic cells and TSE pathogenesis. A comprehensive summary of present TSE diagnostic efforts can be found on the internet (http:www.mad-cow.org/00/sci__archive__frame.html).

Current TSE research has so far failed to implicate Erythroid Differentiation Related Factor (EDRF) or erythroid hematopoietic cell biology in TSE pathogenesis, or identify a non-PrP$^{Sc}$ molecular marker of TSE infection in spleen, blood or bone marrow. Most researchers in the field appear to be focusing on methods aimed at the detection of PrP$^{Sc}$.

It has now been discovered that EDRF, a gene normally expressed in erythroid cells of hematopoietic tissues, is differentially expressed in hematopoietic tissues of TSE infected animals. EDRF is expressed in hematopoietic cells of the erythroid and megakaryocyte/platelet lineage, in spleen, bone marrow and blood. It would therefore appear that hematopoiesis, in particular erythropoiesis, is surprisingly affected in individuals affected by TSE infection.

According to a first aspect of the present invention there is provided a method of diagnosis for the presence of a transmissible spongiform encephalopathy (TSE) in an animal, comprising assaying a sample obtained from the animal to determine the relative number of hematopoietic cells of the erythroid, megakaryocyte or platelet lineages in the sample.

Transmissible Spongiform Encephalopathies (TSEs) or Prion diseases include Scrapie in sheep, Bovine Spongiform Encephalopathy (BSE) in cattle and Kuru, Creutzfeldt-Jacob Disease (CJD), new-variant (nv) CJD, Gerstmann-Straussler Sheinker Syndrome (GSS) and Fatal Familial Insomnia in humans. The TSE diseases are characterized by the deposition of Prion protein$^{Sc}$ (PrP$^{Sc}$), an abnormal isoform of a host-encoded glycoprotein, PrP$^C$. Conversion of normal, proteinase K-sensitive PrP$^C$ into the abnormal, proteinase K-resistant isoform, PrP$^{Sc}$ is recognised characteristic of a TSE disease.

For the purposes of the present invention the term TSE infection is used equivalently to the term TSE disease condition. The exact means by which a TSE disease is transmitted is still the subject of scientific controversy. Experimental animals can be "infected" with a TSE disease in the laboratory. While the clinical manifestations are clear enough, whether the diseases encountered in practice are "infections" in the normal sense of the word is not yet known.

Animals affected by TSE disease include mammals, such as ovines, bovines, humans, felines, elk, deer, mink, and exotic zoo species such as Nyala, Arabian Oryx, Cheetah and greater Kudu, and avian species, such as poultry, for example chickens, turkey, guinea fowl. Methods in accordance with the present application therefore extend to a method of diagnosis for a TSE in sheep, bovines, deer, elk or humans The sample to be assayed according to the present invention typically will be a biological sample, for example a blood-based sample or from a source of hematopoietic cells. The sample may be whole or fractionated blood (or partly fractionated blood), plasma, a hematopoietic tissue, such as bone marrow, or from the spleen. The sample may be subject to the addition of further components so as to optimize sample analysis. For example, in samples of blood, it may be convenient to add substances such as heparin, EDTA and/or sodium citrate to prevent coagulation by means of clot formation. Other sample sources include cerebrospinal fluid (CSF), urine, tears, milk, semen, mucous secretions, tissue or organ biopsies, e.g. brain, liver, thymus, pancreas.

Hematopoietic cells of the erythroid lineage, include pluripotent stem cells, myeloid stem cells, CFU-GEMM cells (Colony-Forming Unit Granulocyte/Erythrocyte/Monocyte/Megakaryocyte), BFU-E cells (Blast-Forming Unit—Erythroid), CFU-E cells (Colony-Forming Unit—Erythroid proerythroblasts), reticulocytes and erythrocytes. The hematopoietic cells of the erythroid lineage are shown schematically in FIG. 13.

A unipotential hematopoietic cell is a cell committed to a single cell lineage; a bipotential hematopoietic cell is a cell committed to one of two possible cell lineages, for example the E/Meg or erythrocyte/megakaryocyte cell which is capable of differentiating along either the erythrocyte or megakaryocyte cell lineages; a tripotential hematopoietic cell is a cell committed to one of three possible cell lineages.

The maturation of an erythrocyte from a proerythroblast includes progression through the following recognized cell types, as described by the Junquiera or the Wheater definitions, as follows:

| Junquiera Definition | Wheater Definition |
|---|---|
| Proerythroblast | Proerythroblast |
| Basophilic Erythroblast | Early Normoblast |
| Polychromatophilic Erythroblast | Intermediate Normoblast |
| Orthochromatophilic Erythroblast | Late Normoblast |
| Reticulocyte | Reticulocyte |

Hematopoietic cells of the mekaryocyte and platelet lineages include the E/Meg precursor cell, the megakaryoblast and the differentiated megakarocyte or platelet cells.

Methods in accordance with the present invention may therefore be directed to an assay for one or more of the above cell types of the hematopoietic erythroid, megakaryocyte, or platelet lineages or expression products associated with one or more the cell types of the hematopoietic erythroid, megakaryocyte, or platelet lineages.

One expression product associated with the cells of hematopoietic erythroid lineage is Erythroid Differentiation Related Factor (EDRF). EDRF is expressed in bipotent cells capable of proceeding through erythroid or megakaryocyte lineages or E/Meg cells, blast-forming unit (BFU-E) cells, colony-forming unit (CPU-E) cells, proerythroblasts (rubriblasts), early normoblasts (basophilic erythroblasts or prorubricytes), intermediate erythroblasts (rubricytes or polychromatophilic erythroblasts), late normoblasts (metarubricytes or orthochromatophilic erythroblasts), including haemoglobin-positive normoblasts and reticulocytes, i.e. cells throughout erythrogenesis, including erythrocytes.

Particular cells of interest which normally express EDRF can be identified using the anti-TER-119 antibody, namely TER-119$^+$cells. TER-119 antibody is raised against the immunogen C57BL/6 mouse day-14 fetal liver cells (Ikuta et al Cell 62 863–874 (1990)) and is of the isotype rat (Wistar) IgG$_{2b}$,κ (TER-119 antibody available from BD Pharmingen, San Diego). The TER-119 antibody reacts with cells of the erythroid lineage in all erythroid-producing organs and with most of the cells that express EDRF, although not all of such cell types. The TER-119 antigen is specifically expressed on erythroid cells form the early erythroblast through mature erythrocyte stages, but not on cells with CFU-E or BFU-E activities. Cells that can be assayed in this way in methods of the present invention include the proerythroblasts, basophilic erythroblasts, polychromatophilic erythroblasts, orthochromatophilic erythroblasts, reticulocytes (primitive erythrocytes) and erythrocytes. Alternative antibodies useful in characterizing such cells are anti-Glycophorin A, anti-EDRF, anti-CD-61, anti-CD-71, anti-transferrin, anti-ferritin, anti-EDRF and anti-haemoglobin antibodies. Anti-CD-61 antibodies can be used to detect cells of the megakaryocyte/platelet lineages from precursors to mature cells (commercially available from Miltenyibiotec—www.miltenyibiotec.com).

In a preferred embodiment of this aspect of the invention, the method of diagnosis comprises assaying for the number of cells of the hematopoietic erythroid, megakaryocyte or platelet lineages that express EDRF. Such cells can include, but are not limited to, E/Meg, CFU-GEMM cells, BFU-E cells, CFU-E cells, proerythroblasts, basophilic erythroblasts, polychromatophilic erythroblasts, orthochromatophilic erythroblasts, reticulocytes (primitive erythrocytes). The depletion of a cell lineage normally expressing EDRF is indicative of a TSE infection (or TSE disease condition) in a subject. The depletion of a cell lineage is in relation to the numbers of cells of the class assayed for which are present in non-infected individuals, in other words a significant deviation from the normal numbers of particular cell. A normal range can be identified by assaying a statistically relevant population of healthy non-infected individuals.

Another expression marker may be hemoglobin which also appears to be depleted in subjects suffering from a TSE infection or TSE disease condition.

The measurement of cell numbers in a sample may be carried out using any convenient method. For example, cell numbers can be assayed using fluorescence-activated cell sorting (FACS); manual counting by means of specific cell stains, e.g. Geimsa-Wright histology stain. Alternatively, automated haematology analysers can be used which can be set to count numbers of hematopoietic cells, such as erythrocytes or reticulocytes (Miltenyibiotec—www.miltenyibiotec.com). It is also possible to assess the number of cells in a sample using a hematocrit, for example routinely used for measurement of erythrocyte numbers, packed cell volume etc. Another method to estimate the number of progenitor cells is to culture blood/bone marrow in a semi-solid medium, such as methyl cellulose, and counting colonies.

The identification of hematopoietic cells of interest using an antibody can use a modified version of the antibody, for example an antibody conjugated with biotin, or with an antibody labelled with a fluorescent marker. Cells that are positive for the antibody of interest can be separated using fluorescence-activated cell sorting (FACS), flow-cytometry or magnetic-bead separation method as convenient. For example cells of the erythroid lineage can be identified using an antibody such as the TER-119 antibody which can be coupled to a suitable reporter moiety.

Establishing a control or normal population value is possible using standard techniques of sample collection and analysis, for example haematology and/or cytology. Standard statistical techniques can be used in order to define meaningful average values for a population which may require taking into account factors such as age, sex and/or genotype, and may be based on an uninfected individual or a population of uninfected individuals.

A recent comparison of blood counts in venous, fingertip and arterial blood (Yang, et al, *Clin. Lab. Haem.* 23 155–159 (2001)) established that normal blood cell population counts in a defined human population were as follows:

| | |
|---|---|
| Leucocyte count | 6.89 (+/− 1.74) × $10^9$ per litre |
| Erythrocyte count | 4.75 (+/− 0.48) × $10^{12}$ per litre |
| Platelet count | 222 (+/−35) × $10^9$ per litre |
| Haemoglobin concentration | 14.3 (+/− 1.4) g/dl |

In a preferred embodiment of this aspect of the invention, the method of diagnosis comprises assaying for the relative concentration of EDRF in sample including cells of the hematopoietic erythroid, megakaryocyte or platelet lineages that express EDRF. Such cells can include, but are not limited to, E/Meg, GEMM cells, BFU-E cells, CFU-E cells, proerythroblasts, basophilic erythroblasts, polychromatophilic erythroblasts, orthochromatophilic erythroblasts, reticulocytes (primitive erythrocytes), megakaryocytes or platelets. The nucleotide sequences of murine, human and bovine EDRF are shown in FIG. 3 and the predicted amino acid sequences are shown in FIG. 4. The relative concentration of EDRF can be assayed directly by measuring the levels of EDRF protein in the sample, or indirectly by using EDRF cDNA to measure levels of mRNA encoding EDRF which is indicative of the level of EDRF expression in cells in the sample. A reduction in levels of EDRF in the sample is indicative of TSE infection (or a TSE disease condition) in a subject. Reduction in expression levels is in relation to the expression levels which are present in non-infected individuals. A normal range can be identified by assaying a statistically relevant population of healthy non-infected individuals.

Further diagnostic assays can involve the use of antibodies to EDRF which can be polyclonal antibodies or monoclonal antibodies. Polyclonal antibodies can be raised by stimulating their production in a suitable animal host (e.g. a mouse, rat, guinea pig, rabbit, sheep, chicken, goat or monkey) when the substance of the present invention is injected into the animal. If necessary an adjuvant may be administered together with the substance of the present invention. The antibodies can then be purified by virtue of their binding to EDRF or as described further below. Monoclonal antibodies can be produced from hybridomas. These can be formed by fusing myeloma cells and spleen cells which produce the desired antibody in order to form an immortal cell line. This is the well known Kohler & Milstein technique (*Nature* 256 52–55 (1975)).

Techniques for producing monoclonal and polyclonal antibodies which bind to a particular protein are now well developed in the art. They are discussed in standard immunology textbooks, for example in Roitt et al, *Immunology* second edition (1989), Churchill Livingstone, London.

In addition to whole antibodies, the present invention includes derivatives thereof which are capable of binding to EDRF. Thus the present invention includes antibody fragments and synthetic constructs. Examples of antibody fragments and synthetic constructs are given by Dougall et al in *Tibtech* 12 372–379 (September 1994). Antibody fragments include, for example, Fab, F(ab')$_2$ and Fv fragments (see Roitt et al [supra]). Fv fragments can be modified to produce a synthetic construct known as a single chain Fv (scFv) molecule. This includes a peptide linker covalently joining $V_h$ and $V_i$ regions which contribute to the stability of the molecule.

Other synthetic constructs include CDR peptides. These are synthetic peptides comprising antigen binding determinants. Peptide mimetics may also be used. These molecules are usually conformationally restricted organic rings which mimic the structure of a CDR loop and which include antigen-interactive side chains. Synthetic constructs also include chimaeric molecules. Thus, for example, humanised (or primatised) antibodies or derivatives thereof are within the scope of the present invention. An example of a humanised antibody is an antibody having human framework regions, but rodent hypervariable regions. Synthetic constructs also include molecules comprising a covalently linked moiety which provides the molecule with some desirable property in addition to antigen binding. For example the moiety may be a label (e.g. a detectable label, such as a fluorescent or radioactive label) or a pharmaceutically active agent.

The antibodies or derivatives thereof specific for EDRF have a variety of other uses. They can be used in purification and/or identification of EDRF itself or a cell that expresses EDRF. As a result they may be used in a diagnostic method according to the present invention.

After the preparation of a suitable antibody to EDRF, it may be isolated or purified by one of several techniques commonly available (for example, as described in *Antibodies: A Laboratory Manual,* Harlow and Lane, eds. Cold Spring Harbor Laboratory Press (1988)). Generally suitable techniques include peptide or protein affinity columns, HPLC or RP-HPLC, purification on Protein A or Protein G columns, or combinations of these techniques. Recombinant antibodies to EDRF can be prepared according to standard methods, and assayed for specificity for EDRF using procedures generally available, including ELISA, ABC, dot-blot assays etc.

An example of one method of assaying for EDRF protein expressed in a sample is western blotting. An extract of proteins from the sample can be fractionated through denaturing SDS-polyacrylamide gel electrophoresis. The mixture can then be transferred and immobilized on a solid membrane of nitrocellulose or nylon by electroblotting. The loaded membrane is then incubated with anti-EDRF antibody. The resulting antigen-antibody complex can then be detected by any suitable procedure. For example, a second antibody, raised against the anti-EDRF antibody, to which a reporter moiety has been linked (for example horseradish peroxidase, alkaline phosphatase) can be added. The reaction product generated by enzyme action can then be used to indicate the position of the target protein on the membrane. Measurement of the levels of enzyme reaction is indicative of the levels of target protein present in the sample. The sensitivity of the detection system can be improved by using the biotin-streptavidin system or by chemiluminescent detection.

Alternatively, levels of EDRF protein can be assayed for by the standard techniques of radio-immunoassay (RIA) or Enzyme-linked immunosorbent assay (ELISA). Antibody is linked to a reporter enzyme and then immobilized on a microtitre plate. A lysate of a sample to be measured is then added to allow antibody-antigen complex formation. After washing and provision of substrate, levels of product formation are proportional to the levels of antigen, i.e. target protein, present in the sample. Another method is the DELFIA system based on a time-resolved fluorometric assay. The Delfia Research System (Wallac) measures the fluorescence of metals from the lanthanide series, including europiun, samarium, and terbium, when chelated to molecules that fluoresce. Antibodies are labelled and immobilized on microtitre plates. A lysate from the sample to be measured is added to the plate to allow antibody-antigen complex formation. After washing, signal is determined.

The presence of RNA transcripts encoding EDRF ready for expression can be assayed for using northern blotting (Thomas, P. S., *Proc. Nat'l Acad. Sci. USA* 77 5201–5205 (1980)). Briefly, denatured RNA from sample cells is transferred onto a nitrocellulose or nylon filter for subsequent use in a hybridisation assay. The RNA is electrophoresed in a denaturing agarose gel before being transferred onto a membrane either by capillary action or under the action of an electrical field. A radioactively labelled DNA or RNA probe specific for EDRF RNA is hybridised to the filter-bound RNA to enable detection. Alternatively, RNA levels can be measured using "taqman™" which is a real-time quantitative RT-PCR procedure whose specificity derives from the use of a fluorescence energy transfer (FRET) probe, or by the "invader" technology based on the discovery of a unique class of structure specific endonuclease enzymes (cleavases). Invader and signal probes are designed to hybridise to overlapping sites on the target DNA/RNA such that the invader probe displaces a portion of the signal probe. This forms a structure that a cleavase enzyme will recognise and cut, thus creating detectable products.

This aspect of the invention can alternatively be defined as a method of diagnosis for the presence of a transmissible spongiform encephalopathy (TSE) in an animal, comprising assaying a sample obtained from the animal to determine the number of haematopoietic cells of the erythroid, megakaryocyte or platelet lineages in the sample relative to a control or normal population value.

According to a second aspect of the present invention there is provided a method of diagnosis for the presence of a transmissible spongiform encephalopathy (TSE) in an animal, comprising assaying a sample obtained from the animal to determine the relative amount in the sample of an expression product of a hematopoietic cell of erythroid, megakaryocyte or platelet lineages. The expression product of a hematopoietic cell of erythroid, megakaryocyte or platelet lineages to be assayed can be as described above. Methods for sample analysis and detection of expression product can be as described above.

The presence of a TSE in an individual can be established by means of this assay without reference to the actual number of hematopoietic cells in the sample, in which the amount of expression product is compared to a normal range identified by assaying a statistically relevant population of healthy non-infected individuals.

According to a third aspect of the present invention there is provided a kit for the diagnosis for the presence of a transmissible spongiform encephalopathy (TSE) in an animal, where the kit comprises an antibody to a cell of the hematopoietic erythroid, megakaryocyte or platelet lineages or an antibody to EDRF. In alternative embodiments of this aspect of the invention, the kit may comprise antibodies to both a cell of the hematopoietic erythroid, megakaryocyte or platelet lineages and to EDRF. Such dual antibody kits may allow for greater sensitivity of the diagnostic method.

Antibodies specific to cells of the hematopoietic erythroid, megakaryocyte or platelet lineages are as described above. Antibodies to EDRF can be made as described above.

Assays for the binding of antibody to target can be performed using standard techniques commonly available such as ELISA, ABC, dot-blot assays. Additional detection labels such as fluorescent or radioactive markers may also be used.

As discussed above, the tissue sources from which samples may be assayed can include blood, or fractions thereof, or other tissues and/or organs. Thus a method of the present application may find utility in pre-screening of blood, (or a fraction thereof), tissue, and/or organs prior to transfusion or transplantation into a recipient. The source of blood, or fractions thereof, or other tissues and/or organs may be allogenic with respect to the recipient, or may be xenogeneic. Where a sample shows a positive result for the presence of a TSE infection using a method according to the first aspect of the invention, this will enable a decision to be taken to avoid using donated blood, (or a fraction thereof), tissue, and/or organs from the individual whose sample was analysed in subsequent transfusion or transplantation into a recipient. By such means, a potential route of TSE infection into the general population may be avoided.

Alternatively, the screening may carried out on samples of blood, (or a fraction thereof), tissue, and/or organs prior to the preparation of a blood or tissue or organ-based product. Such products may include blood plasma or concentrates of blood clotting factors, such as for example, Factor IX, Factor XI, Factor VII, Factor XII, Factor V, Factor XIII, Factor VIIIC, Factor VIIIvWFAg, or hormones such as growth hormone, erthropoietin, thyroxin or insulin prepared from whole blood or another tissue source.

According to a fourth aspect of the invention there is therefore provided a method for the preparation of a blood product, the method comprising assaying a sample of blood for the presence of a transmissible spongiform encephalopathy (TSE) in the animal from which the sample was obtained, in which the assay comprises determining the relative number of hematopoietic cells of the erythroid, megakaryocyte or platelet lineages in the sample.

In a preferred embodiment of the present invention, the method of diagnosing for the presence of a transmissible spongiform encephalopathy (TSE) in the animal, the method may be performed as follows.

sample collection, including optional sample preparation step (e.g. addition of blood clot formation inhibitors; preservative etc.)

determining the relative number of hematopoietic cells of the erythroid, megakaryocyte or platelet lineages in the sample by (a) direct measurement of cell population in sample, or (b) indirect measurement with reference to an expression product of such cell lineages (for example, EDRF protein or RNA encoding EDRF protein).

An example of such a preferred method may comprise the steps of:

(1) sample collection and/or preparation from tissue source;

(2) optionally label cells in sample prior to counting of cell numbers;

(3) determination of the number of hematopoietic cells of the erythroid, megakaryocyte or platelet lineages in the sample by either
 (i) determination by manual counting; or
 (ii) determination by automatic counting; and (4) comparing result with control reference sample from normal uninfected individual.

An alternative method may comprise the steps of:
(1) sample collection and/or preparation from tissue source;
(2) isolation of sample of cells of hematopoietic cells of the erythroid, megakaryocyte or platelet lineages
(3) assay levels of expression products in cells, for example in assaying levels of EDRF expression, either
   (i) determine levels of EDRF protein (e.g. by Western blotting, radioimmunoassay (RIA), or ELISA); or
   (ii) determine levels of mRNA using cDNA probe (e.g. by Northern blotting, or RT-PCR)
(4) comparing result with control reference sample from normal uninfected individual.

Control reference samples from a normal uninfected individual may include pooled samples from a population of normal uninfected individuals sufficient to establish a normal range or normal value in statistical analysis.

In a method according to the present invention, the number of hematopoietic cells of the erythroid, megakaryocyte or platelet lineages can be assessed with respect to an expression product of such cells. The expression product can be a protein, or polypeptide, or it can be the mRNA molecule encoding the protein or polypeptide.

In a method according to the invention, the diagnosis of a TSE infection in an individual being assayed can be made where the result of the assay shows a reduction in the number of cells of hematopoietic cells of the erythroid, megakaryocyte or platelet lineages relative to a control or normal population value.

A control or normal population value may be established as described above and can be based on an uninfected individual or a population of uninfected individuals.

Preferred features for the second and subsequent aspects of the invention are as for the first aspect mutatis mutandis.

The present invention will now be further described with reference to the following Figures and Examples, which are present for the purposes of illustrating the invention and are not to be construed as being limiting. Reference is made to the following figures.

FIG. 3 shows nucleic acid sequence of murine and human full-length EDRF cDNAs and bovine partial EDRF sequence. Full-length (a) (SEQ ID NO: 2) murine and (b) (SEQ ID NO: 3) human EST cDNA clones were obtained through the Human Genome Mapping Project via the IMAGE consortium (IMAGE IDs 466407 and 220221 respectively). cDNA EST clones were sequenced in a forward and reverse direction. (c) (SEQ ID NO: 4) Partial 167 bp sequence of bovine EDRF synthesised following nested PCR with degenerate oligonucleotides as stated in experimental background.

FIG. 4 shows amino acid sequence of Mouse (SEQ ID NO: 5) and Human EDRF (SEQ ID NO: 6) and partial bovine EDRF protein sequence (SEQ ID NO: 7).

FIG. 5 shows assignment of mouse EDRF and TEL to the same genomic locus and analysis of transcript orientations. (a) Southern blot of mouse genomic DNA digested with various restriction endonucleases and probed with radiolabelled full length mouse EDRF cDNA; (b) northern blots of various mouse tissue RNA probed with radiolabelled single-stranded in vitro-transcribed riboprobes.

Figure 6:
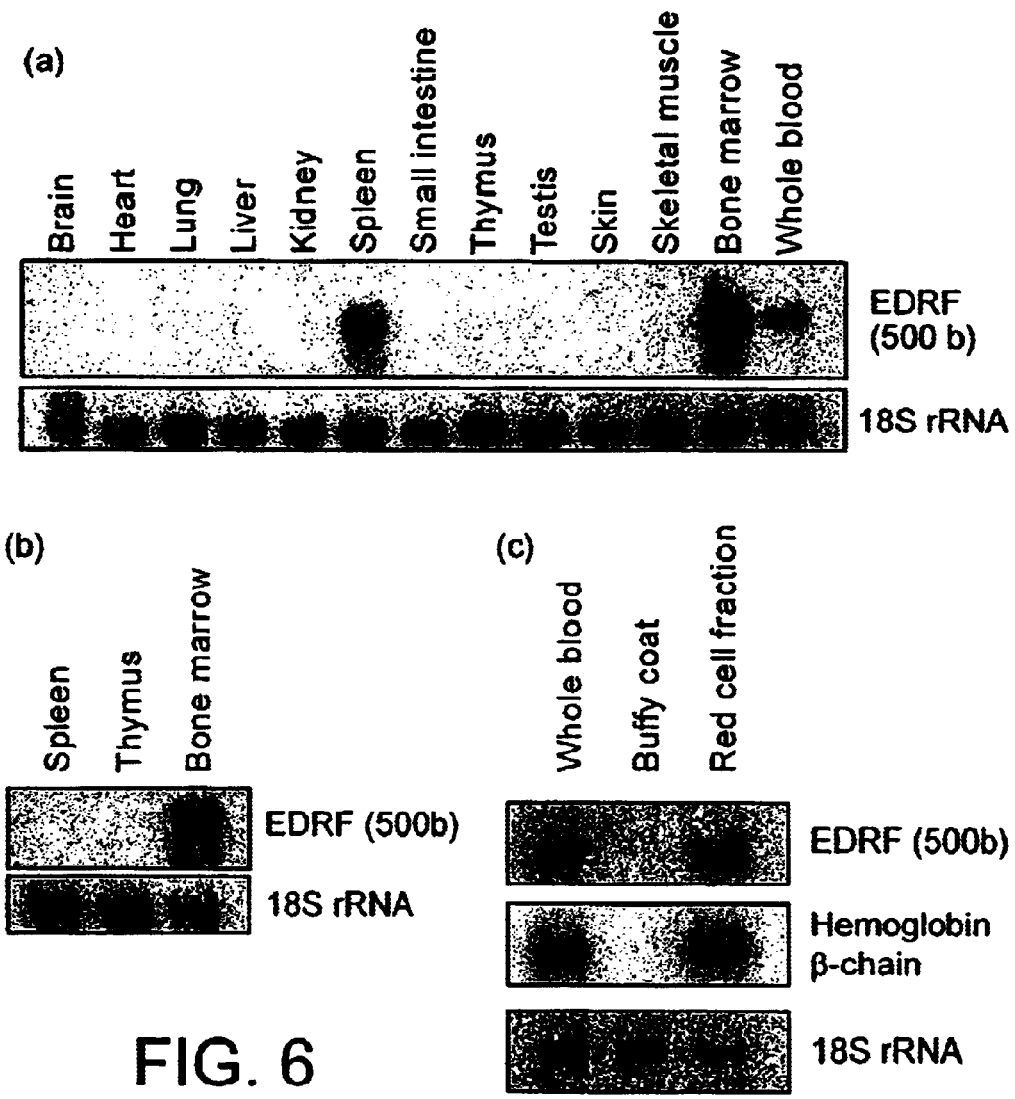

FIG. 6 shows tissue distribution of mouse and human EDRF mRNA expression. Northern analysis of various (a) mouse and (b,c) human tissues was performed with mouse and human radiolabelled cDNA probes.

Figure 7:
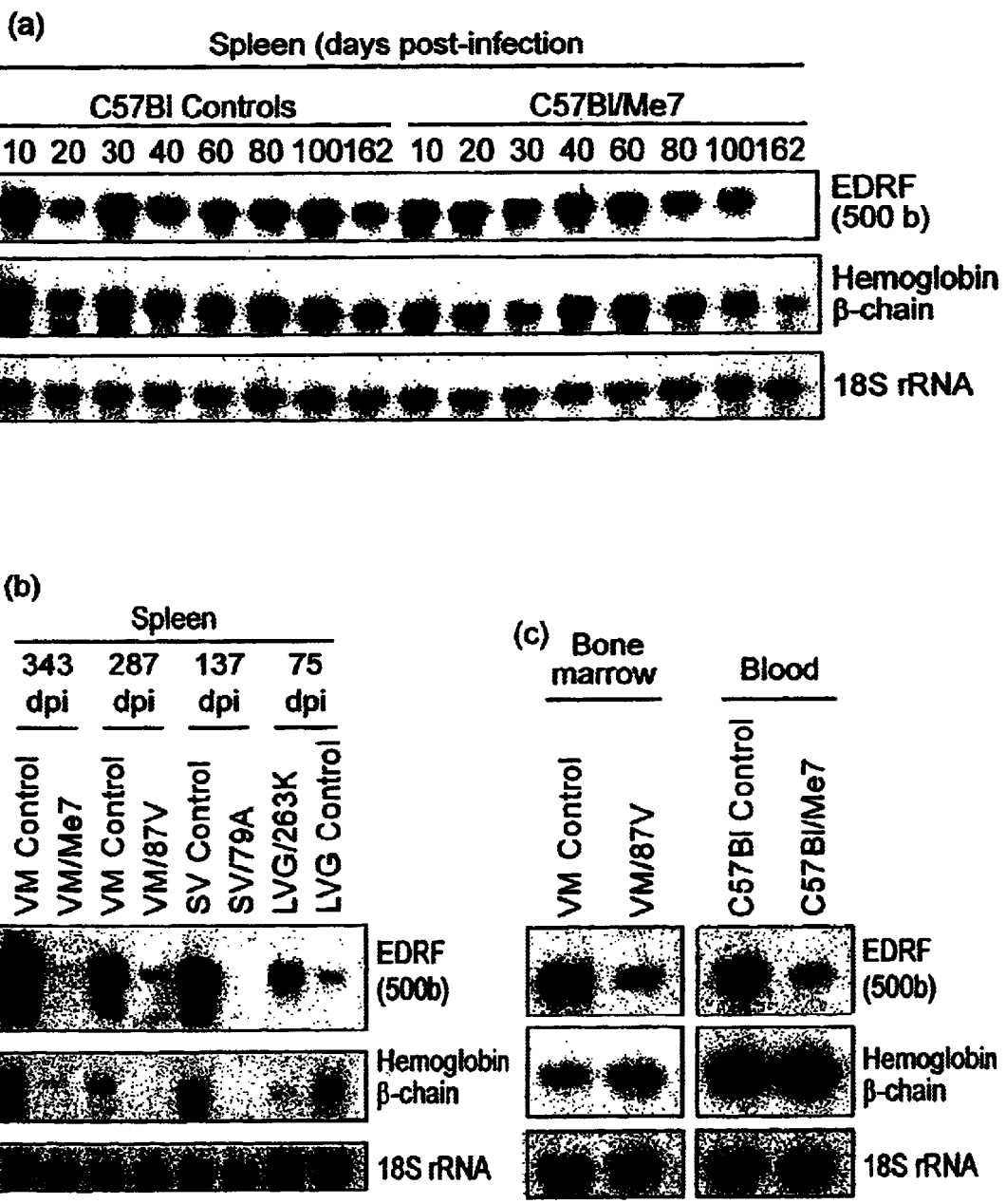

FIG. 7 shows northern analysis of EDRF expression in control and scrapie-infected spleen, bone marrow and whole blood. (a) RNA isolated from control and scrapie infected (Me7 strain) mouse (C57B1 line) spleens at various stages of disease pathogenesis; (b) spleens from various control and scrapie-infected inbred mouse lines (VM and SV) and hamsters (LVG). Scrapie strains were Me7, 87V, 79A and 263K and incubation periods of these models are indicated; (c) bone marrow and whole blood from control and scrapie infected mice (bone marrow; VM mice/87V scrapie strain, whole blood; C57B1 mice/Me7 scrapie strain).

FIG. 8 shows northern analysis of EDRF expression in blood and bone marrow of natural field cases of TSE disease (a) Sheep were age, breed and sex-matched and were of the same PrP genotype (ARQ heterozygotes). Control and scrapie sheep blood was sampled at the same time; (b) EDRF expression in sternum bone marrow of pathologically confirmed BSE-affected cattle culled at first apparent signs of BSE and healthy control.

FIG. 9 shows determination of murine hematopoietic cell lineages that express EDRF.

Figure 10:
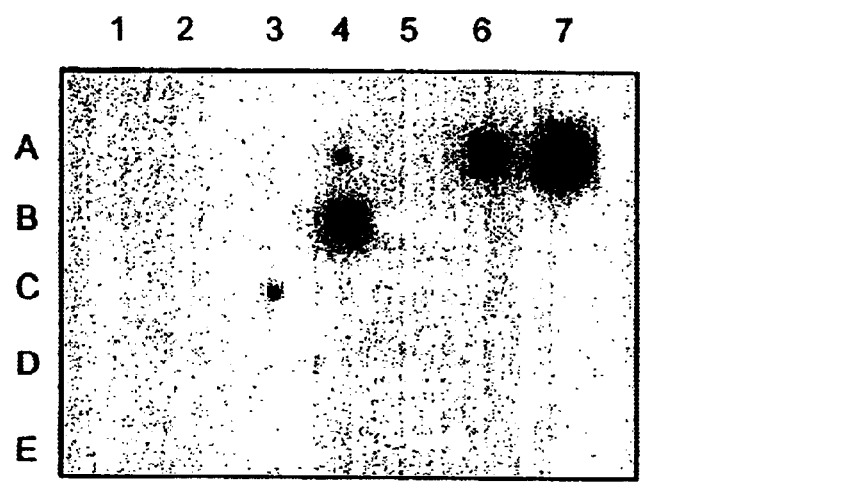

FIG. 10 shows further characterization of hematopoietic cells which express EDRF. Abbreviations are as followed: E, hemoglobin-positive normoblasts and reticulocytes; Meg, megakaryocytes; Mac, macrophages; Neut, neutrophils; Mast, mast cells; BFU-E, precursor-producing colonies containing erythrocytes; CFU-E, hemoglobin-negative cells at proerythroblast/CFU-E stage.

FIG. 11 shows assignment of EDRF expression to hematopoietic cells committed to the erythroid lineage. (a) EDRF RNA expression in bone marrow suspensions depleted of specific cell lineages. Lane A; untreated whole bone marrow. Lanes B to G represents bone marrow suspensions depleted of $CD3e^+$, $CD11b^+$, $CD45R/B220^+$, $Ly-6G^+$, $TER-119^+$ and Lineage-negative (stem) cells respectively; (b) & (c) Schematic representation of hematopoietic cell hierarchy. Abbreviations: Meg, megakaryocyte; E, erythroid; Mast, mast cells; Mac, macrophage, Neut, neutrophil; B, B-cells; T, T-cells; p, progenitor; BFU-E/CFU-E, blast- and colony forming unit, erythroid progenitor.

Figure 12:
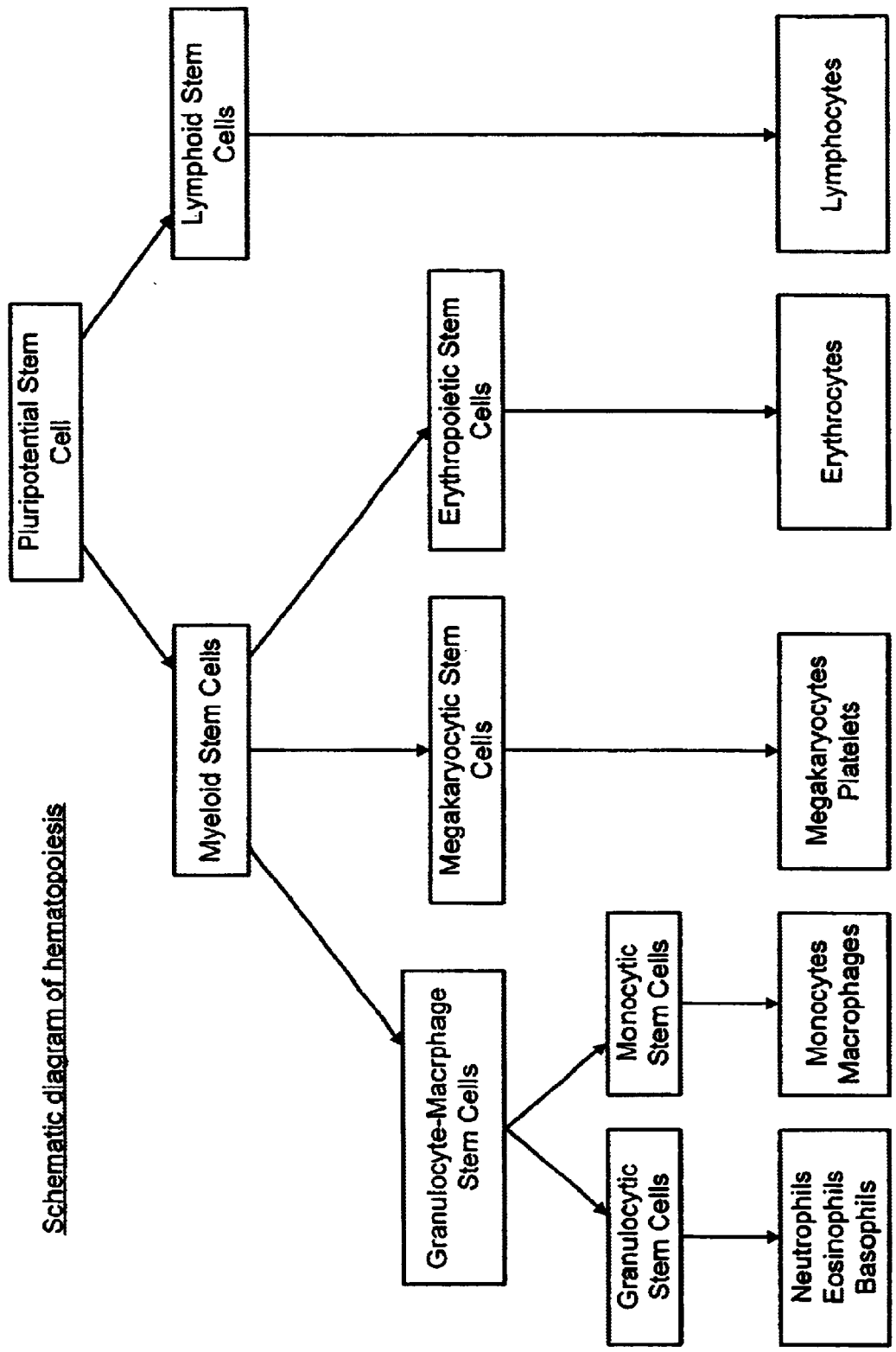

FIG. 12 which shows a diagram of hematopoiesis.

Figure 13:
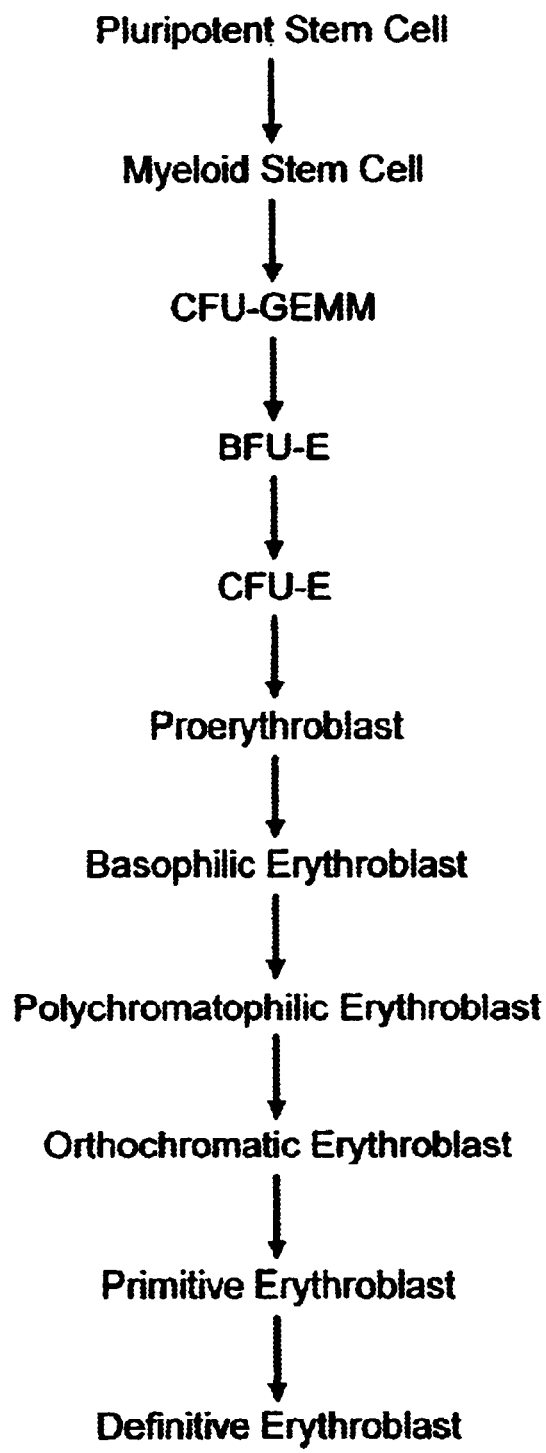

FIG. 13 which shows a diagram of the hematopoietic cells of the erythroid lineage.

MATERIALS AND METHODS

All tissues from TSE infected mice were obtained from the Neuropathogenesis Unit (NPU), Edinburgh. Blood from control and natural sheep scrapie cases were obtained from the NPU. Tissues from field cases of BSE were obtained from the MAFF Central Veterinary Laboratory (CVL), Weybridge. Human RNA was purchased from Clontech, UK. Antibodies reactive against mouse hematopoietic cells were purchased from Beckton Dickinson, UK. Davids Biotechnologie, Germany, have been contracted to synthesise mouse and human Erythroid Differentiation Related Factor (EDRF) peptides and produce antisera against these peptides. Human and Mouse full-length EDRF cDNAs were obtained free-of-charge through the Human Genome Mapping Project (UK) via the IMAGE consortium Hematopoietic cell cDNA dot-blot was a donation from Norman Iscove (Canada).

EXAMPLE 1

Analysis of Gene Expression

The well characterized Me7 strain of scrapie was intracerebrally injected into C57B1 mice as a model of TSE infection. Age and sex matched mice were intracerebrally injected with 20 μl of a 1:10 w/v of normal brain homogenate. Brains and spleens were collected from control and TSE-infected animals at 10, 20, 30, 40, 60, 80, 100 and 162 days post-injection (dpi). 162 dpi represents the terminal stage of disease in this model. Total RNA was isolated from 'pooled' tissues and used as template to synthesise cDNA subpopulations for subsequent Differential Display Reverse-Transcriptase Polynerase Chain Reaction (DDRT-PCR). DDRT-PCR is a powerful molecular tool which allows visualisation of gene expression in any particular cell type or tissue via the creation of RNA fingerprints. Genes which are differentially expressed between two or more samples under study are readily identifiable and recoverable using this technique. DDRT-PCR analyses were performed essentially as previously described (Liang et al Science 257 967–971 (1992)) with modifications (Miele et al BioTechniques 25 (1) 138–144 (1998)). Using DDRT-PCR technology, the genes expressed in the spleens of mice at various stages of TSE disease pathogenesis were compared with genes expressed in control spleens. Bands representing differentially expressed cDNAs were recovered and cloned as previously described (Miele et al In "Expression Generics", eds McClelland & Pardee, pages 433–444, Natick:Eaton Publishing (1999)(a)); Miele et al Prep. Biochem. Biotech. 29 (3) 245–255 (1999)(b)). Cloned cDNAs were sequenced and identified following computer-assisted homology searching of the public nucleotide and protein databases. Cloned cDNAs were used for radiolabelling for use as probes in Northern and Southern hybridisation studies according to standard protocols (Sambrook et al "Molecular Cloning: A Laboratory Manual", New York: Cold Spring Harbor Laboratory Press (1989)).

To clone a region of bovine EDRF nucleic acid sequence for use as a homologous probe to bovine sequences, the Polymerase Chain Reaction (PCR) was performed using the following degenerate oligonucleotide primers (SEQ ID NOS: 8–10) and bovine genomic DNA as template. Primers were designed on the basis of open reading frame homology between mouse and human EDRF.

infected mice at the latter stages of disease pathogenesis (FIG. 1). cDNA representing this transcript was recovered from the DDRT-PCR gel, purified, PCR re-amplified and cloned into the pBluescript II SKII+ cloning vector (Stratagene).

Figure 1:
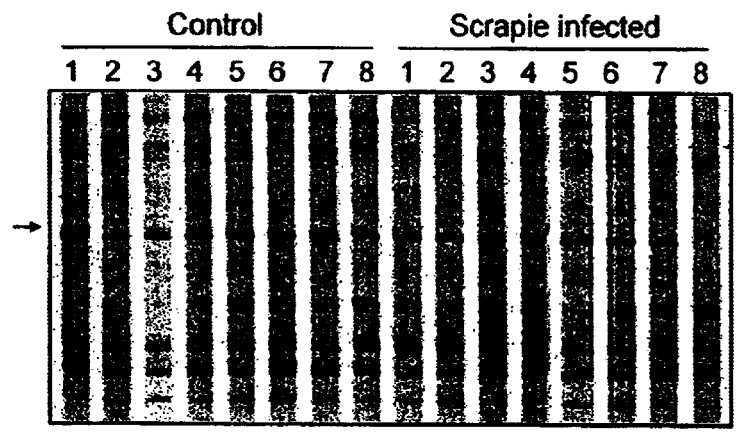
FIG. 1 shows a panel from a DDRT-PCR gel comparing a subset of expressed genes in spleens of age and sex matched control and scrapie infected mice (intracerebral route) at various stages of disease pathogenesis. 1, 10 days post-infection (dpi); 2, 20 dpi; 3, 30 dpi; 4, 40 dpi; 5, 60 dpi; 6, 80 dpi; 7, 100 dpi; 8, 162 dpi (terminal).

The results in FIG. 1 show a panel from a DDRT-PCR gel comparing a subset of expressed genes in spleens of age and sex matched control and scrapie infected mice (intracerebral route) at various stages of disease pathogenesis. 1, 10 days post-infection (dpi); 2, 20 dpi; 3, 30 dpi; 4, 40 dpi; 5, 60 dpi; 6, 80 dpi; 7, 100 dpi; 8, 162 dpi (terminal). cDNA representing this transcript dow regulated in scrapie infected spleens was recovered and cloned into pBluescript KSII+ (Stratagene) as previously described (Miele et al BioTechniques 25 (1) 138–144 (1998); Miele et al In "Expression Genetics", eds McClelland & Pardee, pages 433–444, Natick:Eaton Publishing (1999)(a)); Miele et al Prep. Biochem. Biotech. 29 (3) 245–255 (1999)(b)).

Standard DNA sequencing, followed by computer-assisted homology searches of the public nucleotide and protein databases revealed that this cDNA represented a fragment of the 505 nucleotide Mouse void Differentiation Related Factor mRNA (mEDRF, Genbank accession AF055085, AF060220). This gene has been described only in the public nucleotide databases However, in addition to matching mEDRF with 100% homology, the DDRT-PCR cDNA fragment also has a 100% match at the nucleic acid level with a small region of the much larger mouse TEL oncogene (Genbank accession NM007961.1). In fact, the full 505 nucleotide mEDRF cDNA sequence matches mouse TEL cDNA 100% in an antisense orientation (See FIG. 2).

Figure 2:
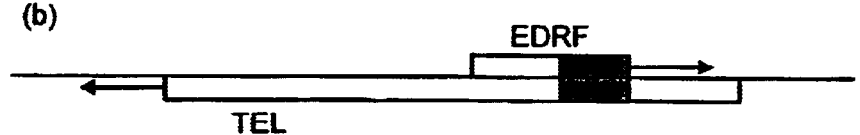
FIG. 2 shows sequence (SEQ ID NO: 1) identity of cDNA isolated from DDRT-PCR gel shown in FIG. 1.

FIG. 2 shows sequence identity of cDNA isolated from DDRT-PCR gel shown in FIG. 1. cDNA has a 100% match at nucleotide level to positions 263 to end of 505 nucleotide Mus Musculus Erythroid Differentiation Related Factor mRNA (mEDRF). However, it also has a 100% match to positions 796 to 582 of Mus Musculus ets variant gene 6 (TEL oncogene) in an antisense orientation. Positions of DDRT-PCR primers are underlined. (b) Detailed computer-assisted analysis of both EDRF and TEL transcripts indicate

```
ED1F;   5'-CA(AG)CA(AG)GT(AGCT)TT(CT)(AG)A(CT)GA(CT)CC-3'
        (SEQ ID NO:8)

ED3F;   5'-GA(AG)GA(AG)GA(CT)ATGGT(AGCT)A(CT)(AGCT)GT-3'
        (SEQ ID NO:9)

ED2R;   5'-AG(AG)AAIIIIC(GT)(AG)TA(CT)TT(AGCT)GC(AGCT)A-3'
        (SEQ ID NO:10)
```

First-round PCR was performed using standard concentrations of reagents and ED1F and ED2P, primers, and cycled 40 times at 94° C. for 1 minute, 50° C. for 1 minute and 72° C. for 1 minute. 1 μl of PCR product was used under the same conditions as for first-round PCR, with the exception that ED3F and ED2R primers were used for nested PCR. A DNA PCR product of the expected size of 168 bp was gel-purified and cloned into the T/A cloning vector pGEM-Teasy (Promega). Plasmid DNA isolated from several clones was sequenced in a forward and reverse orientation and a consensus partial open reading frame sequence for bovine EDRF compiled.

The source material for this analysis was spleen tissue pooled from control and from scrapie (Me7 strain) infected mice (intracerebral route of inoculation) at various defined stages of disease pathogenesis. One transcript was identified which appeared downregulated in the spleens of TSE-that both transcripts are encoded on the same genomic locus, but run antisense to each other. Hatched box represents the schematic position of the sequence indicated in (a). Genbank accession numbers are as follows: Mouse EDRF (AF055085, AF060220), Mouse TEL NM007961.1). Clones representing full-length human and mouse EDRF cDNAs were obtained through the Human Genome Mapping Project, Hinxton, Cambridge (IMAGE clone identities 230221 and 466407 respectively).

EXAMPLE 2

Cloning of Bovine EDRF Sequence

The DDRT-PCR EDRF cDNA fragment referred to above does not represent the entire EDRF cDNA sequence. The fall-length mouse and human EDRF cDNA clones (IMAGE IDs 230221 and 466407 respectively) were obtained free-of-charge from the Human Genome Mapping Project, Cambridge. These full-length cDNAs were sequenced in both directions and the sequence information is presented in FIG. 3. To obtain a homologous probe for bovine EDRF RNA, for fixture use as a probe in expression studies, degenerate PCR (See Materials & Methods) was performed on bovine genomic DNA. A PCR product of the expected size was purified and cloned into the pGEMT-easy vector (Promega). The nucleotide sequence of these clones is presented in FIG. 3. Sequence analysis confirms that this partial DNA sequence represents the open reading frame region of the bovine homolog of mouse and human EDRF.

FIG. 3 shows nucleic acid sequence of murine and human full-length EDRF cDNAs and bovine partial EDRF sequence. Full-length (a) murine and (b) human EST cDNA clones were obtained through the Human Genome Mapping Project via the IMAGE consortium (IMAGE IDs 466407 and 220221 respectively). cDNA EST clones were sequenced in a forward and reverse direction. (c) Partial 167 bp sequence of bovine EDRF synthesised following nested PCR with degenerate oligonucleotides as stated in experimental background. Variant nucleotides (conservative amino acid substitutions) are underlined. At the nucleotide level, mouse and human EDRF cDNA sequences are 72.2% identical over 403 nucleotides. The bovine EDRF partial DNA sequence matches from positions 153 To 318 of mouse EDRF cDNA and 171 to 337 of human EDRF cDNA. At the nucleotide level, bovine EDRF is 78.4% identical to human and 75.6% identical to mouse EDRF sequences over 167 nucleotides.

EXAMPLE 3

Raising Antisera to EDRF Proteins

Utilising the human, mouse and partial bovine EDRF cDNA sequences presented in FIG. 3, the amino acid sequences encoded by these sequences was deduced (See FIG. 4). Davids Biotechnologie (Germany) are synthesising peptides from the mouse and human conceptual EDRF proteins and raising antisera following immunization of chickens.

FIG. 4 shows amino acid sequence of Mouse and Human EDRF and partial bovine EDRF protein sequence. Sequences are conceptual translations based on nucleotide sequences of full-length mouse and human EDRF cDNAs and partial bovine open reading frame DNA sequence (nucleotide sequences shown in FIG. 3). Peptides underlined in a & b represent those chosen to contract Davids Biotechnologie (Germany) to synthesise and immunise chickens for the production of antibodies to human and mouse EDRF proteins. At the amino acid level, human and mouse EDRF proteins are 63.7% identical and the bovine partial EDRF protein (55 amino acids) is 72.7% identical to human and 67.3% identical to mouse EDRF proteins. Note that variant bovine EDRF nucleotides indicated in FIG. 3 result in conservative amino acid substitutions, with the exception of codon 6, which may be isoleucine or threonine.

EXAMPLE 4

Relationship between TEL & EDRF

On the basis of computer-assisted sequence alignments, EDRF appears to be encoded on the DNA strand antisense to TEL. It is important to establish whether the transcript identified as being differentially expressed in TSE-infected spleen (FIG. 1) represents EDRF or TEL. Preliminary Southern-blot analysis with the full-length mEDRF probe indicates that EDRF and TEL are likely to be encoded on the same genomic locus (FIG. 5). However, Northern analysis, using single-stranded riboprobes, reveals that the approximate 500 nucleotide EDRF transcript is the RNA which is underrepresented in TSE-infected mouse spleen (Me7 spleen) and that TEL is undetectable under these conditions (EDRF sense riboprobe—antisense to TEL RNA). These experiments formally prove that the transcript identified as being differentially expressed by DDRT-PCR is mEDRF.

FIG. 5 shows assignment of mouse EDRF and TEL to the same genomic locus and analysis of transcript orientations. (a) Southern blot of mouse genomic DNA digested with various restriction endonucleases and probed with radiolabelled full length mouse EDRF cDNA. The approximate 505 bp EDRF cDNA nucleic acid sequence is 100% identical to TEL. The detection of single bands for each restriction digest indicates that EDRF and TEL are likely to be encoded on the same genomic locus. Mouse EDRF cDNA contains an EcoRI site and should result in the detection of two bands following probing with mEDRF full-length EDNA if EDRF and TEL were encoded on the same genomic locus. (b) To further investigate indications from nucleic acid sequence analysis that TEL and EDRF transcripts) encoded on the same genomic locus, are antisense to each other, northern blots of various mouse tissue RNA were probed with radiolabelled single-stranded in vitro-transcribed riboprobes. EDRF RNA is detected only using the EDRF antisense riboprobe (TEL sense riboprobe). This indicates that EDRF is in fact a transcript antisense to TEL and not an alternatively spliced transcript of TEL. TEL RNA is not detectable under these conditions using the TEL antisense riboprobe. EDRF and TEL transcripts therefore differ significantly with regard to size, orientation and abundance. Taqman RT-PCR analysis has revealed that, unlike EDRF, TEL RNA is not differentially expressed in scrapie-infected mouse spleen.

EXAMPLE 5

Tissue Distribution of EDRF RNA Expression

Northern analysis of a wide variety of murine tissues demonstrates that EDRF is expressed only in mouse spleen, bone marrow and whole blood, with bone marrow representing the tissue with the highest levels of EDRF transcript (FIG. 6a). Note that EDRF expression is undetectable in thymus, indicating that EDRF expression is not associated with lymphocytes. In adult mice, these tissues represent tissues of hematopoietic activity, and, with the exception of thymus, erythropoiesis. In human tissues (RNA purchased from Clontech), EDRF is expressed in bone marrow, but not in spleen (FIG. 6b). In humans, bone marrow is the major tissue of hematopoietic activity. EDRF is also expressed in human whole blood (FIG. 6c). Analysis of human blood buffy coat (containing lymphocytes) and non-lymphocyte fraction indicates that EDRF expression in blood is associated with red cells and not lymphocytes.

FIG. 6 shows tissue distribution of mouse and human EDRF mRNA expression. Northern analysis of various (a) mouse and (b,c) human tissues was performed with mouse and human radiolabelled cDNA probes. (a) Mouse EDRF is expressed only in spleen, bone marrow and whole blood. (b,c) Human EDRF is expressed only in bone marrow and whole blood. These tissues are hematopoietic tissues (spleen, bone marrow and blood in mice and bone marrow and blood in humans). EDRF expression correlates with tissues which express hemoglobin (expressed only in erythroid cells). 18S rRNA probing indicates equivalent loading of RNA in all lanes. (c) Northern analysis of EDRF in human blood buffy coat and red cell fractions indicates that EDRF expression is associated with fractions enriched for erythroid cells, as indicated by subsequent hemoglobin detection.

EXAMPLE 6

EDRF Expression in Tissues from Rodent Experimental TSE Diseases

The expression of EDRF in spleens from mice at various stages of TSE disease pathogenesis (Me7 scrapie strain) was studied. As shown in FIG. 7a, EDRF is dramatically downregulated in the spleens of mice at the terminal stages of TSE disease compared to mock-infected controls. This downregulation is apparent at approximately on third of the way through disease pathogenesis in spleen. Hemoglobin β-chain is also downregulated in spleens of mice at terminal stages of disease. Further studies demonstrated that EDRF downregulation is also apparent in spleens from rodents at the terminal stages of disease pathogenesis from other experimental TSE diseases, as is hemoglobin β-chain (FIG. 7b). Additionally, this effect is apparent in a hamster model of TSE infection (LVG hamsters, 263K scrapie strain). Therefore, EDRF and hemoglobin β-chain differential expression in spleen is a feature common to these various models of TSE disease. Since EDRF is also expressed in bone marrow and whole blood of mice, it was investigated whether EDRF is differentially expressed in these tissues in TSE-infected mice. As shown in FIG. 7c, EDRF is also downregulated in bone marrow and blood of mice at the terminal stages of disease pathogenesis analysed. However, in contrast to results obtained from mouse spleen, hemoglobin β-chain is not differentially expressed in bone marrow or blood from scrapie infected mice.

FIG. 7 shows northern analysis of EDRF expression in control and scrapie-infected spleen, bone marrow and whole blood. (a) RNA isolated from control and scrapie infected (Me7 strain) mouse (C57B1 line) spleens at various stages of disease pathogenesis. EDRF is profoundly downregulated in scrapie-infected mouse spleen at terminal stages (162 dpi) of disease pathogenesis compared to controls. This downregulation is detectable at earlier stages. Hemoglobin β-chain RNA is also downregulated in scrapie-infected mouse spleen. (b) Confirmation that EDRF downregulation is apparent in other rodent models of TSE disease. Spleens from various control and scrapie-infected inbred mouse lines (VM and SV) and hamsters (LVG). Scrapie strains were Me7, 87V, 79A and 263K and incubation periods of these models are indicated. Both EDRF and hemoglobin β-chain are profoundly downregulated in spleen from a variety of rodent genotypes following infection with a variety of scrapie strains. This also demonstrates that the discovery of EDRF downregulation is not a phenomenon limited to mice. (c) EDRF is also expressed in bone marrow and whole blood (see FIG. 5), therefore bone marrow and whole blood from control and scrapie infected mice (bone marrow; VM mice/ 87V scrapie strain, whole blood; C57B1 mice/Me7 scrapie strain) was studied to determine whether EDRF was also differentially expressed in tissues from scrapie-infected mice. EDRF is downregulated in bone marrow and whole blood from scrapie-infected mice at terminal stages of disease pathogenesis. In contrast to spleen, hemoglobin β-chain RNA is expressed at similar levels in bone marrow and blood from scrapie-infected mice at terminal stages of disease. 18S rRNA probing confirms similar RNA loading in all lanes. At terminal stages of disease pathogenesis, EDRF is downregulated in spleen (>30-fold), bone marrow (8-fold) and whole blood (4-fold). All samples were obtained from mice following infection via intracerebral injection.

These results demonstrate for the first time a molecular difference between infected and uninfected animals in hematopoietic tissues.

EXAMPLE 7

EDRF Expression in Tissues From Natural Field Cases of TSE Disease

Whether the observed effects of TSE infection on EDRF expression in hematopoietic tissues is a phenomenon peculiar to experimental rodent models, or is common to other, natural, TSE diseases was investigated further. Whole blood was obtained from sheep displaying early clinical signs of natural scrapie (1.5 months prior to death from disease). Control material was sampled from age, breed and sex-matched sheep of the same PrP genotype (PrP genotype being a factor which is well known to influence susceptibility to disease). Northern analysis of RNA isolated from ovine whole blood using a radiolabelled full-length human EDRF cDNA detected an approximate 3.5 Kb transcript which is underrepresented in blood of natural field-case scrapie (FIG. 8a). Re-probing of this Northern blot with the partial bovine EDRF cDNA hybridises to the same transcript. Therefore, although the detected ovine transcript is significantly larger than mouse or human EDRF, this transcript does in fact represent the ovine EDRF RNA. Spleen and sternum bone marrow was also obtained from healthy cattle and cattle suspected of suffering from BSE (and which were subsequently pathologically confirmed to have BSE). Control and BSE cattle were breed-matched, non-pregnant females approximately similar ages (>3.5 years old). Northern analysis utilising the partial bovine EDRF cDNA has demonstrated that the bovine EDRF transcript is approximately the same size (approximately 500 nucleotides) as mouse and human EDRF. It has been found that, like humans, cattle do not express EDRF in spleen. However, analysis of sternum bone marrow reveals that bovine EDRF is dramatically downregulated in animals displaying signs of BSE (FIG. 8a) as it is in the bone marrow of mice experimentally infected with the TSE agent.

FIG. 8 shows northern analysis of EDRF expression in blood and bone marrow of natural field cases of TSE disease. (a) Sheep were age, breed and sex-matched and were of the same PrP genotype (ARQ heterozygotes). Control and scrapie sheep blood was sampled at the same time. Scrapie sheep blood was obtained approximately one and a half months prior to death from disease, from sheep that were displaying early clinical signs of scrapie. Southern analysis of human, cattle and sheep genomic DNA indicated that human EDRF cDNA was a suitable probe to cattle and sheep sequences (not shown). The Northern blot was therefore probed with a radiolabelled human and bovine EDRF cDNA. Human blood RNA serves as a positive control for the experiment. Phosphorimager analysis reveals that the putative sheep EDRF RNA is downregulated approximately 50% in blood of sheep at early stages of clinical signs of natural scrapie (animal relatively healthy at this stage). Using the bovine partial EDRF cDNA as a probe hybridises to the same transcript, further indicating that this 3.5 Kb transcript is a true ovine EDRF homolog. (b) EDRF expression in sternum bone marrow of pathologically confirmed BSE-affected cattle culled at first apparent signs of BSE and healthy control. Cattle were breed-matched females, non-pregnant and approximately the same age (>3.5 years old).

The Northern blot was probed with radiolabelled partial bovine EDRF cDNA. Bovine EDRF RNA is approximately the same size as mouse and human EDRF RNA and is dramatically downregulated in the bone marrow of cattle suffering from natural BSE. These experiments demonstrate that EDRF as an indicator of prion disease is applicable in natural field cases of prion disease and that EDRF differential expression is not a phenomenon peculiar to experimentally induced prion disease in rodents.

These experiments clearly show that EDRF differential expression, and perhaps some aspect of dysfunction of the hematopoietic cell types expressing EDRF) are features common to both experimental and natural field cases of TSE disease.

EXAMPLE 8

Determination of Hematopoietic Cell Types which Express EDRF

EDRF is clearly a novel useful pre-mortem marker and indicator of TSE infection. It is possible that the observed EDRF differential expression represents an effect of the expression of this gene, or it indicates the progressive loss/depletion of the hematopoietic cell types which are associated with EDRF expression. As a first step to resolving this issue, the hematopoietic cell types which express EDRF have been further defined A panel of antibodies reactive against distinct murine hematopoietic cell lineages was obtained (Pharmingen/Beckton Dickinson). These antibodies were used to deplete whole bone marrow cell suspensions of various hematopoietic lineages. RNA was then isolated from the remaining cells and EDRF expression assessed by Northern analysis. Loss of EDRF expression in any particular fraction would indicate that the cells that had been removed were those which express EDRF. As can be seen from FIG. 9, EDRF expression is dramatically reduced in bone marrow which has been depleted of TER-119 positive cells, as is hemoglobin β-chain expression. The TER-119 antibody reacts with hematopoietic cells at all stages of erythroid development, with the exception of early BFU-E or CFU-E progenitors.

FIG. 9 shows determination of murine hematopoietic cell lineages that express EDRF. EDRF is expressed only in murine spleen, bone marrow and whole blood (see FIG. 5). Lack of detectable signal in either mouse or human thymus indicates that EDRF expression is not associated with T- or B-cells, as does lack of detectable signal in buffy coat fraction of human blood (see FIG. 5). To determine which hematopoietic cell lineages express EDRF, mouse bone marrow cell suspensions were enriched for non-committed stem cells or specific cell populations were depleted using a panel of antibodies (purchased from Pharmingen) and CEL-Lection biotin binding dynabeads (purchased from Dynal). RNA was subsequently isolated and used for Northern analysis with a radiolabelled mouse EDRF cDNA probe. EDRF signal is significantly reduced only in RNA from the cell suspension depleted of erythroid cells. As predicted, hemoglobin β-chain RNA is also reduced in this fraction. The TER-119 antibody does not react with committed erythroid cells possessing BFU or CFU activities (BFUe/CFUe). Detectable EDRF expression in RNA from fraction enriched for non-committed hematopoietic stem cells likely represents EDRF expression in BFUe and CFUe erythroid cells but the possibility of EDRF expression in non-committed stem cells can not be ruled out at present. Similarly, EDRF expression can be detected in TER-119 positively-selected hematopoietic cells. However, expression can also be detected in other lineages at a lower level (CD3+, CD11b+, CD45R+, B220+, Ly-6G+ cells). EDRF expression is therefore predominantly associated with hematopoietic cells of the erythroid lineage, but is also expressed in other, non-B/non-T cell, hematopoietic cells. However, hemoglobin expression in this fraction indicates that erythroid cells are co-purifying with the other lineages. EDRF is likely to be expressed only in the erythroid lineage. Further characterization of the cell lineage of EDRF expression is presented in FIG. 10. It has yet to be determined whether the discovered downregulation of EDRF expression in scrapie-infected spleen, bone marrow and blood represents a specific gene-effect or, as seems more likely given the downregulation of hemoglobin in spleen, whether this downregulation is caused by depletion of erythroid cells.

These results indicate that EDRF expression is associated primarily with erythroid cells, and the reduction of hemoglobin P-chain expression in the same TER-119 cell depleted fraction substantiates this.

For confirmation, a positive selection experiment was performed and clearly, EDRF expression (and hemoglobin) is associated with TER-119 enriched fractions. BFU-E and CFU-E cells remain in the cell fraction that also contains pluripotent, non-committed hematopoietic stem cells. Apparent EDRF expression in enriched TER-119 negative and BFU-B/CFU-E negative cells is clearly due to contamination since hemoglobin is also detectable in these preparations. EDRF is clearly also present in RNA isolated from the mixed population of BFU-E/CFU-E and stem cells. However, it was unclear which of these progenitor cell types express EDRF. In order to clarify this, a dot-blot was obtained containing amplified cDNA synthesised from RNA which had been isolated from hematopoietic cells at defined stages of development (donated by Norman Iscove, Canada).

FIG. 10 shows further characterization of hematopoietic cells which express EDRF. Abbreviations are as follows: E, hemoglobin-positive normoblasts and reticulocytes; Meg, megakaryocytes; Mac, macrophages; Neut, neutrophils; Mast, mast cells; BFU-E, precursor-producing colonies containing erythrocytes; CFU-E, hemoglobin-negative cells at proerythroblast/CFU-E stage. For example, E/Meg/Mac indicates a multipotential progenitor cell capable of developing through the erythroid, megakaryocyte or macrophage lineages. Similarly, Mac progenitor indicates a unipotent cell committed to proceeding through the macrophage lineage. EDRF expression was detected in (i) bipotent cells capable of proceeding through erythroid or megakaryocyte lineages, (ii) BFU-E cells, (iii) CFU-E cells and (iv) hemoglobin-positive normoblasts and reticulocytes. Highest EDRF expression was observed in hemoglobin-negative CFU-E erythroid cells. T-cells in this system were obtained from cultures of spleen cells treated with Concanavalin A. These enriched T-cells contain contaminating hemoglobin-positive erythroid cells. Apparent EDRF expression in the T-cell fraction (grid reference C3 is likely to represent the presence of contaminating EDRF-expressing erythroid cells. The lack of EDRF expression in human 'buffy coat' (FIG. 6) substantiates this. EDRF is therefore expressed in all hematopoietic cells committed to proceeding through the erythroid lineage and at all stages or erythroid cell development (including TER- 119+, BFU-E and CFU-E cells) and in cells capable of differentiating along the megakaryocyte/platelet lineage.

As FIG. 10 shows, EDRF expression is associated only with those cells which are committed to the erythroid lineage, including BFU-E and CFU-E cells. Hematopoietic stem cells do not express EDRF. EDRF expression is highest in CFU-E erythroid cells. The earliest stage at which EDRF is detectable, at a low level, in this system is in bi-potential cells which are capable of proceeding through erythroid or megakaryocyte lineages. EDRF is clearly associated with hematopoietic cells of the erythroid lineage.

FIG. 11 shows the assignment of EDRF expression to hematopoietic cells committed to the erythroid lineage. (a) EDRF RNA expression in bone marrow suspensions depleted of specific cell lineages. Lane A; untreated whole bone marrow. Lanes B to G represents bone marrow suspensions depleted of CD3e⁻, CD11b⁺, CD45R/B220⁺, Ly-6G⁺, TER-119+ and Lineage-negative (stem) cells respectively. Mouse bone marrow suspensions were depleted of specific hematopoietic cell lineages using a panel of individual biotin-conjugated antibodies purchased from BD Pharmingen, and streptavidin-coated magnetic beads (Dynal) according to the manufacturers instructions. Antibodies were reactive against the following hematopoietic lineages: CD3e (thymocytes, T-lymphocytes); CD11b (granulocytes, monocytes/macrophages, dendritic cells, natural killer cells and B-1 cells); CD45R/B220 (B-lineage cells from pro-B to mature and activated B-cells); Ly-6G (monocytes, neutrophils, differentiating and maturing granulocytes); TER-119 (all committed cells to the erythroid lineage from early erythroblast through mature erythrocyte stages). (b) & (c) Schematic representation of hematopoietic cell hierarchy. Abbreviations: Meg, megakaryocyte; E, erythroid, Mast, mast cells; Mac, macrophage, Neut, neutrophil; B, B-cells; T, T-cells; p, progenitor; BFU-E/CFU-E, blast- and colony forming unit, erythroid progenitor. (b) EDRF expression is restricted to cells at all stages of erythroid development. (c) PrP RNA expression in hematopoietic cells. Co-expression of EDRF and PrP transcripts occurs in bipotent E/meg cells (indicated by asterisk). Level of expression is indicated by degree of shading, with more intense shading indicating higher levels of expression. Dot-blots of cDNA synthesised from poly(A)+, mRNA purified from individual cells representing 16 stages of the hematopoietic hierarchy were a donation from N. Iscove (University of Toronto, Canada).

SUMMARY OF RESULTS

The present results identify a gene, which encodes a protein of unknown function, that is differentially expressed in hematopoietic tissues of animals suffering from TSE disease. This expression profile of this gene is highly specific, being expressed predominantly, if not exclusively, in hematopoietic cells of the erythroid lineage. This therefore demonstrates a novel, non-PrP$^{Sc}$-based, molecular marker/hallmark of TSE infection that is easily detectable in hematopoietic tissues. This has not been reported previously.

What is claimed is:

1. A method of diagnosis for the presence of a transmissible spongiform encephalopathy in an animal, comprising:
assaying a sample obtained from the animal to determine the relative number of hematopoietic cells of the erythroid, megakaryocyte or platelet lineages in the sample with reference to an expression product of said cells, and
comparing the amount of expression product to a normal range,
wherein the expression product assayed for is Erythroid Differentiation Related Factor and wherein a reduction in the number of cells of a cell lineage normally expressing Erythroid Differentiation Related Factor is indicative of the presence of a transmissible spongiform encephalopathy.

2. A method of diagnosis for the presence of a transmissible spongiform encephalopathy in an animal as claimed in claim 1 in which the transmissible spongiform encephalopathy is Scrapie, Bovine Spongiform Encephalopathy, Chronic Wasting Disease, Creutzfeldt-Jacob Disease, or a new-variant Creutzfeldt-Jacob Disease.

3. A method of diagnosis for the presence of a transmissible spongiform encephalopathy in an animal as claimed in claim 1, in which the sample is whole or fractionated blood, a hematopoietic tissue, such as bone marrow, or from the spleen.

4. A method of diagnosis for the presence of a transmissible spongiform encephalopathy in an animal as claimed in claim 1, in which the hematopoietic cells of the erythroid, megakaryocyte or platelet lineages that are assayed comprise, pluripotent stem cells, myeloid stem cells, CFU-GEMM cells (Colony-Forming Unit Granulocyte/Erythrocyte/Monocyte/Megakaryocyte), BFU-E cells (Blast-Forming Unit—Erythroid), CFU-E cells (Colony-Forming Unit Erythroid), proerythroblasts, reticulocytes, erythrocytes, megakaryocytes, or platelets.

5. A method of diagnosis for the presence of a transmissible spongiform encephalopathy in an animal as claimed in claim 1, in which the hematopoietic cells to be assayed are characterized by reaction to an antibody selected from the group consisting of anti-TER-119, anti-Glycophorin A, anti-CD-71, anti-Erythroid Differentiation Related Factor and anti-hemoglobin antibodies.

6. A method of diagnosis for the presence of a transmissible spongiform encephalopathy in an animal as claimed in claim 5, in which the cells to be assayed are selected from the group consisting of proerythroblasts, basophilic erythroblasts, polychromatophilic erythroblasts, orthochromatophilic erythroblasts, and reticulocytes (primitive erythrocytes).

7. A method of diagnosis for the presence of a transmissible spongiform encephalopathy in an animal as claimed in claim 1, in which the hematopoietic cells to be assayed are characterized by reaction to anti-CD-61 antibodies.

8. A method of diagnosis for the presence of a transmissible spongiform encephalopathy in an animal as claimed in claim 7, in which the cells to be assayed are selected from the group consisting of E/Meg cells, megakaryoblasts, megakaryocytes and platelet cells.

9. A method of diagnosis for the presence of a transmissible spongiform encephalopathy in an animal, comprising:
assaying a sample obtained from the animal to determine the relative amount in the sample of an expression product of a hematopoietic cell of erythroid, megakaryocyte or platelet lineages, and
comparing the amount of expression product to a normal range,
wherein the expression product assayed for is Erythroid Differentiation Related Factor and wherein a reduction in the level of Erythroid Differentiation Related Factor is indicative of the presence of a transmissible spongiform encephalopathy.

10. A kit for diagnosis for the presence of a transmissible spongiform encephalopathy in an animal, wherein the kit comprises:
one or more antibodies to a cell of the hematopoietic erythroid, megakaryocyte or platelet lineages, and
materials for measurement of cell numbers,
wherein the presence of a TSE infection in a sample is indicated by a depletion of a cell lineage normally expressing EDRF.

11. A kit for the diagnosis for the presence of a transmissible spongiform encephalopathy in an animal, wherein the kit comprises:
one or more antibodies to an expression product of a cell of the hematopoietic erythroid, megakaryocyte or platelet lineages, and
materials for assaying for a concentration of expression product,
wherein the presence of a TSE infection in a sample is indicated by a reduction in the amount of expression product, and
wherein the expression product of a cell of the hematopoietic erythroid, megakaryocyte or platelet lineages to which the antibody binds is Erythroid Differentiation Related Factor.

12. A kit as claimed in claim 10, further comprising one or more control population values or ranges.

13. A kit as claimed in claim 11, further comprising one or more control population values or ranges.

* * * * *

UNITED STATES PATENT AND TRADEMARK OFFICE
CERTIFICATE OF CORRECTION

PATENT NO. : 6,962,787 B2  Page 1 of 1
APPLICATION NO. : 09/999305
DATED : November 8, 2005
INVENTOR(S) : Michael Clinton et al.

It is certified that error appears in the above-identified patent and that said Letters Patent is hereby corrected as shown below:

In Claim 4, column 25, line 46, please delete "comprise," and insert the phrase --are selected from the group consisting of--; line 51, please delete the word "or" and insert the word --and--.

Signed and Sealed this

Fifteenth Day of January, 2008

JON W. DUDAS
*Director of the United States Patent and Trademark Office*